(12) United States Patent
Neeper

(10) Patent No.: US 8,636,459 B2
(45) Date of Patent: Jan. 28, 2014

(54) AUTOMATED STORAGE SYSTEM FOR HIGH DENSITY STORAGE

(75) Inventor: Robert K. Neeper, Ramona, CA (US)

(73) Assignee: Brooks Automation, Inc., Chelmsford, MA (US)

( * ) Notice: Subject to any disclaimer, the term of this patent is extended or adjusted under 35 U.S.C. 154(b) by 308 days.

(21) Appl. No.: 13/151,178

(22) Filed: Jun. 1, 2011

(65) Prior Publication Data

US 2012/0003067 A1   Jan. 5, 2012

Related U.S. Application Data

(60) Provisional application No. 61/350,451, filed on Jun. 1, 2010.

(51) Int. Cl.
  *B65G 1/06* (2006.01)
  *B66F 9/075* (2006.01)

(52) U.S. Cl.
  USPC .......................................... 414/280; 414/661

(58) Field of Classification Search
  USPC ......... 414/267, 273, 277, 278, 281, 282, 288, 414/331.08, 331.16, 416.04, 661, 788.4, 414/788.8, 793.3, 797.9
  See application file for complete search history.

(56) References Cited

U.S. PATENT DOCUMENTS

| | | | | | |
|---|---|---|---|---|---|
| 3,240,365 A | * | 3/1966 | King | ............................ | 414/273 |
| 3,492,704 A | * | 2/1970 | Schwellenbach | ............. | 425/162 |
| 3,850,316 A | * | 11/1974 | Schmitt | ......................... | 414/278 |
| 3,927,773 A | * | 12/1975 | Bright | ............................ | 414/273 |
| 4,016,986 A | * | 4/1977 | Thomas | ........................ | 414/198 |
| 4,338,056 A | * | 7/1982 | Abrahamson et al. | ........ | 414/152 |
| 5,125,782 A | * | 6/1992 | Goldschmidt et al. | ........ | 414/276 |
| 5,364,220 A | * | 11/1994 | Killinger | ....................... | 414/272 |
| 5,707,199 A | * | 1/1998 | Faller | ............................ | 414/239 |
| 2005/0260102 A1 | | 11/2005 | Angelantoni et al. | | |
| 2007/0172396 A1 | | 7/2007 | Neeper et al. | | |
| 2009/0044642 A1 | | 2/2009 | Woolley et al. | | |

FOREIGN PATENT DOCUMENTS

| | | | | | |
|---|---|---|---|---|---|
| DE | 3443315 A | * | 8/1985 | | |
| EP | 514613 A1 | * | 11/1992 | | |
| EP | 827692 A1 | * | 3/1998 | | |
| EP | 1757882 | | 2/2007 | | |
| JP | 4-420104 | * | 4/1992 | ............... | B65G 1/04 |
| JP | 08258913 A | * | 10/1996 | | |
| WO | 2009094071 | | 7/2009 | | |

* cited by examiner

*Primary Examiner* — Gregory Adams
(74) *Attorney, Agent, or Firm* — Perman & Green, LLP; Colin C. Durham

(57) ABSTRACT

Within a storage compartment, closely spaced rows of adjacent stacks are supported on a plurality of parallel sliding rails. A pair of coordinated robots is positioned with one robot on one side of the stacks to push the stacks within a selected row toward the other robot. The pushing robot on one side of the row starts off with a starting stack supported in its support arms. The pushing robot pushes the starting stack into one end of the selected row, causing the row to shift toward the waiting receiving robot, which receives the stack at the opposite end of the row from the starting stack. A series of pushes between the two robots moves a stack containing a desired sample into alignment with an access port in the storage compartment.

8 Claims, 13 Drawing Sheets

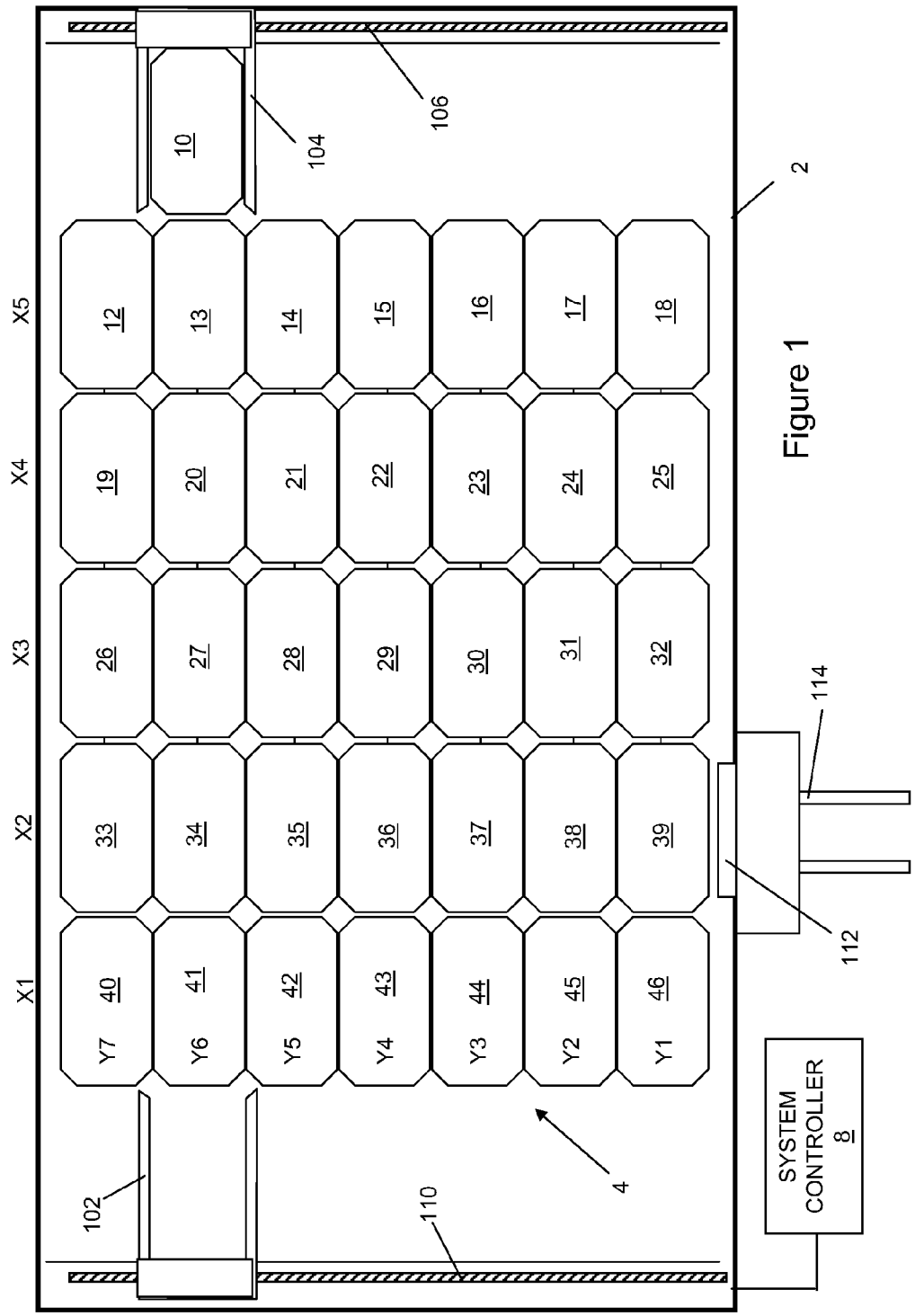

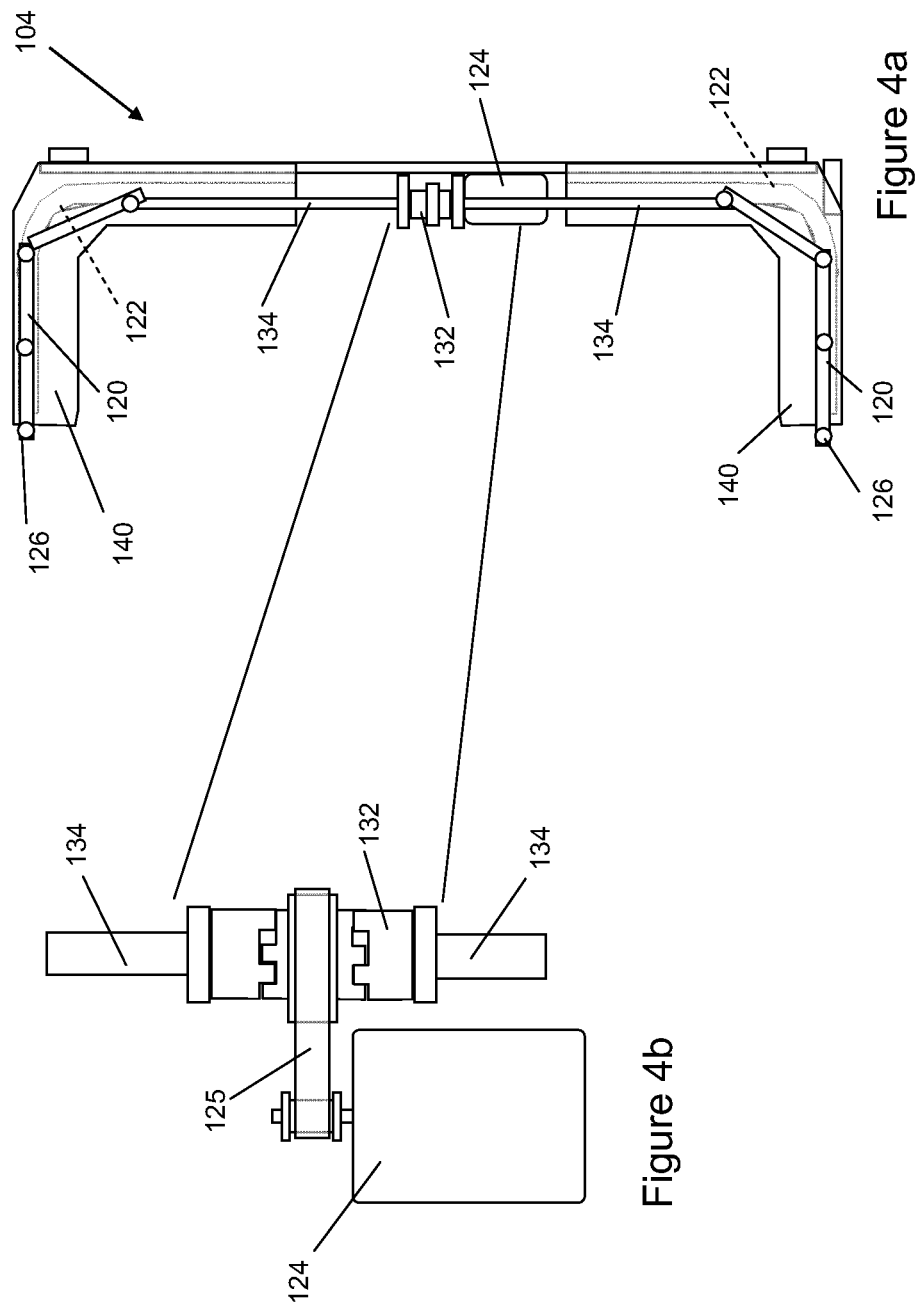

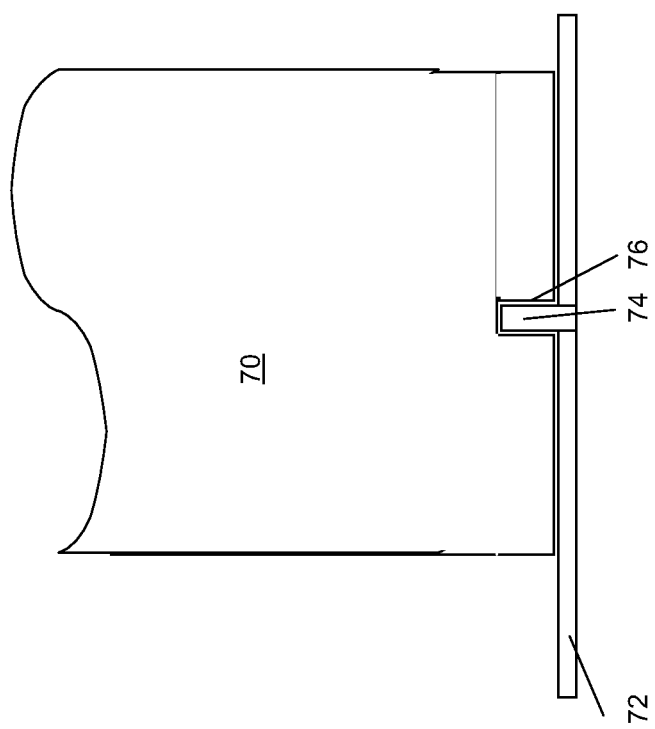

AUTOMATED STORAGE SYSTEM FOR HIGH DENSITY STORAGE

RELATED APPLICATIONS

The present application claims the benefit of the priority of U.S. provisional application No. 61/350,451, filed Jun. 1, 2010, which is incorporated herein by reference in its entirety.

FIELD OF THE INVENTION

The present invention relates to systems for handling and storing biological or chemical samples, and more specifically to an automated system for storage and retrieval of samples retained in sealed arrays of storage containers.

BACKGROUND OF THE INVENTION

Many scientific and medical organizations, including industrial concerns, regulatory agencies, research laboratories, and academic institutions, have the need for secure storage of very large numbers, e.g., a few thousand up to multiple millions, of samples and specimens. Such fields include pharmaceutical, biotechnology, laboratory diagnostics, genomics, biological specimen banks, forensics, agrichemical and specialty chemical. Depending on the application, the sample sizes can vary from tens of microliters to several drams, which are stored in small, sealed plastic tubes or vials. These containers are retained in a rack that allows individual samples to be inserted or removed without removing an entire rack, or the tray the holds one or more racks. To extend the useful lifetime of the samples, they are stored in a controlled environment of low temperature (typically −20° to −80° C. or lower), low humidity, and inert gas (nitrogen), and are subjected to as little environmental variation as possible. In order to handle very large numbers of samples in the most efficient manner, a number of considerations must be made to enhance the system's flexibility and adaptability for different applications with the smallest possible footprint to minimize the use of valuable laboratory space.

An overview of currently available compound storage systems and technologies is provided by Dr. John Comley in his article entitled "Compound Management in pursuit of sample integrity", published in *Drug Discovery World,* Spring 2005, pp. 59-78, which is incorporated herein by reference.

Given the high costs of laboratory space, one area of focus in the design of storage systems in life science is how to make the system more compact while still retaining the ability to quickly access any sample for removal or storage.

A typical automated storage system includes shelves with a robot that moves along an aisle between the shelves to place and retrieve samples. Examples of such "narrow-aisle" storage systems include the SmaRTStore™ and CompactStore™ available from RTS Lifescience, and the HomeBase™ manufactured by TAP (The Automation Partnership). This configuration generally results in a footprint that is about 65% storage and 35% dedicated to robotics.

In order to maximize the functional storage space, the area dedicated to the robotics should be minimized without sacrificing accessibility. The present invention is directed to such a compact storage system.

SUMMARY OF THE INVENTION

The inventive system modifies the conventional narrow aisle approach to sample storage by eliminating the aisle(s) between the shelves, instead storing the samples, typically in plates or trays, in closely spaced rows of adjacent stacks that are supported on a plurality of parallel sliding rails. The external structure (housing) and environmental control systems remain essentially the same as existing systems. The difference lies in the robotic handlers and close-packed arrangement of the storage stacks, providing for much higher storage density.

A pair of coordinated robots is positioned with one robot on one side of the stacks to push the stacks within a selected row toward the other robot. The "pushing" robot on one side of the row starts off with a stack supported in its support arms; this stack may be referred to as the "starting stack". The pushing robot pushes the starting stack into one end of the selected row, causing the row to shift toward the waiting receiving robot, which receives the stack at the opposite end of the row from the starting stack.

The storage compartment is filled with a plurality of stacks that can be configured to hold plates, racks, or tubes. The stacks are slidably mounted within the storage compartment so that they are free to slide left and right within the storage area. Generally, the stacks will move only along the x-axis or only along the y-axis, but not in both directions. Regardless of whether movement is along the x- or y-axis, the pusher robots will be positioned on opposite sides of the axis of movement. The stacks can be arranged in any number of rows or columns (as viewed from the top), but more columns will increase the time to access an individual stack. More rows will not severely affect access time. On the other hand, more columns will increase storage density while more rows will not.

The robotic mechanism on each side of the stacks is adapted to push a stack of trays from one side to the other along a given row. The stacks are preferably designed to slide on wear resistant, low friction plastic or polymer surfaces, such as PTFE (TEFLON®) or similar, without the need for expensive bearings or hardware. Rails or guides are positioned at one or both of the bottom and the top of the stacks to keep the rows aligned as the stacks move.

A computer controller tracks the location of each stack, and each tray in each stack as the stacks are shifted. In a preferred embodiment, to minimize the time required for retrieving multiple samples stored at different locations in the array of stacks, the computer controller may prompt the user to enter all samples that are requested. The controller will identify the requested samples' current locations and determine a sequence of pushes that will bring all requested samples to the access port in the fewest steps.

The pusher mechanisms can be linked (by cables, belts, or electronically) so that each is in the same position front to back. This will ensure that one is ready to receive a stack when pushed by the other.

There must always be one stack more than the array of stacks, with the "odd-stack-out" ("OSO") stack being held by one of the pushers. For example, if the array is 5×7, there would be 36 stacks; for a 6×6 array, there would be 37.

In one aspect of the invention, a storage system for storing a plurality of samples includes a storage compartment having an access port, an array of stacks disposed within the storage compartment, the array of stacks comprising rows and columns of slidable stacks adapted for retaining sample containers, a plurality of guides extending along each row of stacks adapted for sliding the stacks parallel to the rows, a pair of robotic handlers disposed on opposite sides of the array of stacks, each robotic handler having a pushing mechanism, a drive mechanism for moving the pair of robotic handlers in a direction parallel to the columns, and a starter stack retained within a first robotic handler of the pair of robotic handlers, wherein the first robotic handler initiates a first push cycle by pushing the starter stack against a first end of a selected row of stacks so that a second stack on the second end of the row of stacks is received by the second robotic handler, the pair of handlers moves to a different row of stacks where the second robotic handler initiates a second push cycle by pushing the second stack into the second end of the different row, wherein the pair of robotic handlers repeat a plurality of push cycles until a selected stack containing a selected sample is positioned for access at the access port.

In another aspect of the invention, a storage system for storing a plurality of samples includes a storage compartment having an access port, an array of stacks disposed within the storage compartment, the array of stacks comprising rows and columns of slidable stacks adapted for retaining sample containers, a plurality of guides extending along each row of stacks adapted for sliding the stacks parallel to the rows, a first robotic handler and a second robotic handler disposed on opposite sides of the array of stacks, each robotic handler comprising a pushing mechanism, a drive mechanism for moving the first and second robotic handlers between the rows of stacks, a starter stack retained within the first robotic handler, wherein the first robotic handler initiates a push cycle by pushing the starter stack against a first end of a selected row of stacks to displace a second stack from the selected row of stacks into the second robotic handler, and wherein the first and second robotic handlers execute a series of push cycles on different rows of stacks to reposition a selected stack from its starting location to a different location that is accessible from the access port.

BRIEF DESCRIPTION OF THE DRAWINGS

FIG. 1 is a top diagrammatic view of an exemplary arrangement according to the present invention showing an exemplary array of stacks with 5 columns and 7 rows, two pusher robots and an access port.

FIG. 4a is a diagrammatic front view showing the drive details of the pusher arms; FIG. 4b is a diagrammatic detail view of the drive details shown in FIG. 4a.

FIG. 7 is a diagrammatic side view of an exemplary rail structure for guiding movement of the stacks.

DETAILED DESCRIPTION

Figure 2A:
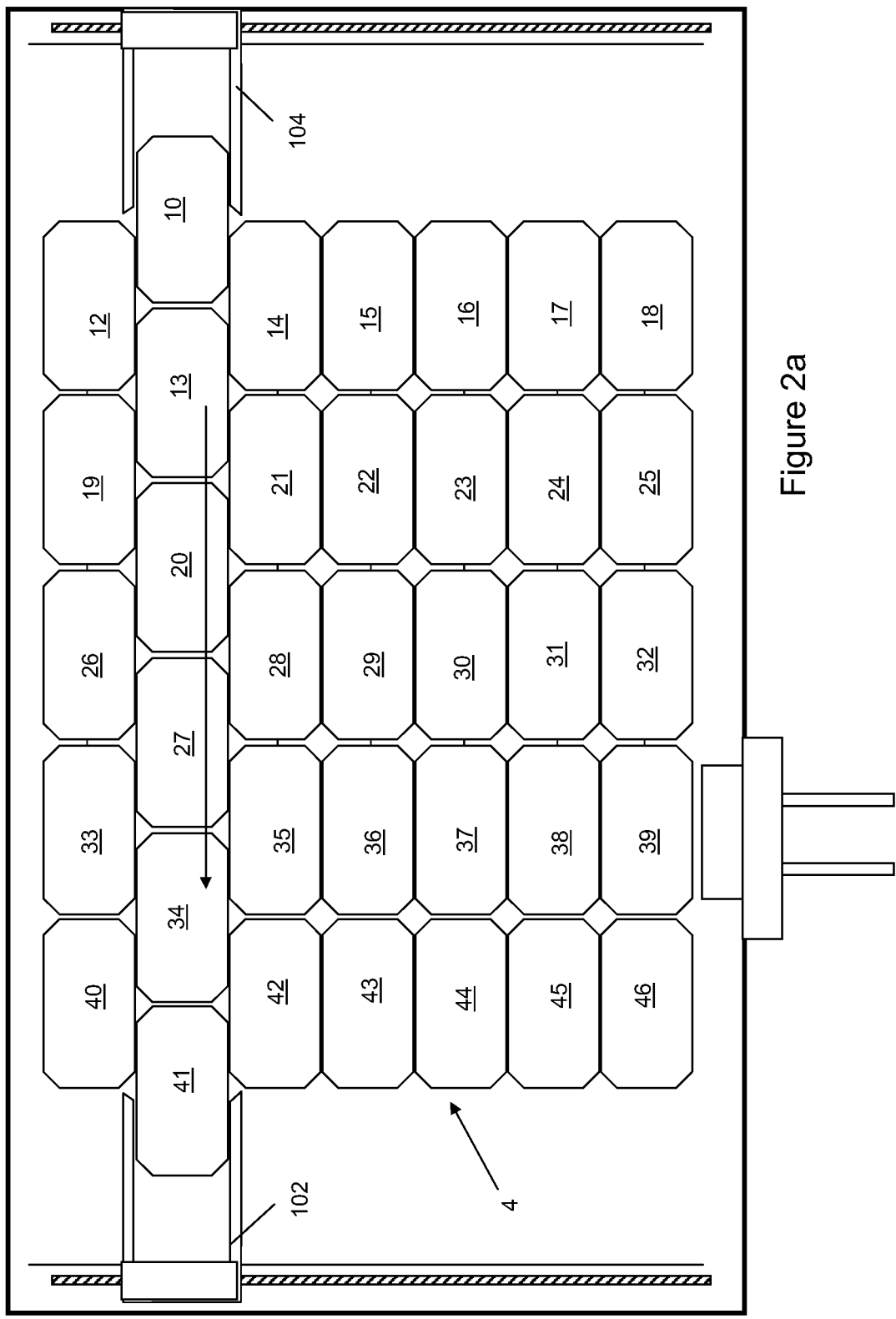
FIGS. 2a-2e are top diagrammatic views of steps in a sequence for moving storage stacks according the present invention.

For purposes of the following detailed description, discussion of specific directions of movement, e.g., left, right, forward, and backward, are made to facilitate understanding of the invention with reference to the exemplary embodiment shown in the figures and are not intended to be limiting.

In the present invention, the external structure (housing) and environmental control systems remain essentially the same as existing systems. The difference lies in the robotic handlers and close-packed arrangement of the storage stacks, providing for much higher storage density.

As shown in FIG. 1, storage compartment 2 encloses an array 4 of storage stacks 12-46 and a pair of coordinated robots 102, 104, which are positioned with one robot on one side of the stack arrays 4 to push the stacks within a selected row toward the other robot. An exemplary array of stacks with 5 columns and 7 rows is illustrated. For reference, the rows are designated as Y1 through Y7 and the columns are designated as X1 through X5. An access port 112 and robotic handler 114 are positioned at the front of the storage compartment 2 to provide for insertion and removal of sample trays or other sample carriers. A system controller 8 provides a user interface for selecting samples to be accessed and for determining a sequence of steps required to efficiently reposition the stack containing a desired sample within reach of the access port 112.

The "pushing" robot 104 starts off with a stack 10 supported in its support arms. As illustrated in FIGS. 1 and 2a stack 10 may be referred to as the "starting stack". It should be noted that the starting stack only refers to the "odd-stack-out" at the snapshot in time at which a pushing sequence is initiated. The stack that is the starting stack will change as transfers occur. Referring to FIG. 2a, the pushing robot 104 pushes the starting stack 10 into the right end of the selected row Y6, causing row Y6 to shift to the left toward the waiting receiving robot 102, which receives stack 41 at the opposite end of row Y6 from the starting stack 10.

The stacks 10, 12-46 in array 4 can be configured to hold plates, racks, or tubes. These stacks are free to slide left and right within the storage area. Generally, the stacks will move only along the x-axis or only along the y-axis, but not in both directions. Regardless of whether movement is along the x- or y-axis, the pusher robots 102, 104 will be positioned on opposite sides of the axis of movement. The stacks can be arranged in any number of rows or columns (as viewed from the top), but more columns will increase the time to access an individual stack. More rows will not significantly affect access time. On the other hand, more columns will increase storage density while more rows will not.

As illustrated in FIG. 7, each stack 70 is configured to slide on low friction, wear resistant plastic or polymer surfaces 72, such as PTFE (TEFLON.RTM.) or similar materials that are known in the art to be self-lubricating, without the need for expensive bearings or hardware. Rails or guides 74 are positioned at one or both of the bottom and the top of the stacks. In the illustrated embodiment, the rails 74 fit within corresponding channels 76 formed in bottom and or top of the stack 70 to keep the rows aligned as the stacks move. Alternative rail arrangements for guiding the movement of the stacks will be readily apparent to those of skill in the art.

A computer controller 8 tracks the location of each stack, and each tray in each stack as the stacks are shifted. In a preferred embodiment, to minimize the time required for retrieving multiple samples stored at different locations in the array of stacks, the computer controller may prompt the user to enter all samples that are requested. The controller 8 will identify each sample's current locations and determine a sequence of pushes that will bring all requested samples to the access port in the fewest steps.

The pusher mechanisms 102, 104 can be linked (by cables, belts, or electronically) so that each is in the same position front to back, i.e., at opposing ends of a row. This will ensure that one is ready to receive a stack when pushed by the other.

There must always be one stack more than the array of stacks, with the "odd-stack-out" ("OSO") stack being held by one of the pushers. For example, if the array is 5×7, there would be 36 stacks as shown in FIG. 1, with the OSO being held by pusher 104.

Referring to FIG. 1, access to the stacks is provided at the front of the compartment 2, as illustrated, and can include an automated plate handling mechanism that removes the plates or trays from the stack, so that the stacks would never need to leave the storage area. Generally, the access port 112 may be positioned at any point on the compartment housing 2 that lines up with a column and row and is sufficiently close to the stack to reach through the housing to remove or replace a tray. As illustrated, the access port 112 is positioned for accessing the stack at column X2, row Y1. The access port 112 is an opening through the compartment housing 2. In one embodiment, the access port 112 may be enclosed within an environmentally-controlled (temperature controlled and/or gas filled) chamber (not shown) in which a load/unload robot 114 operates. The load/unload robot would operate much like a fork lift, with an elevator that travels along the z-axis to access the tray at a predetermined height within the stack once the desired stack has been delivered to column X2, row Y1, which may be referred to as the "access position". To remove a plate, the arms of the fork lift 114 are extended into a space below the desired tray. The fork lift is raised slightly, then retracted to bring the tray through the access port 112 and out of the stack.

FIGS. 2a-2e illustrate a sequence in which a stack in the array is moved into the access position through a series of moves. In the exemplary array, any stack in the array can be brought to the access point in six or fewer moves. A push cycle is defined as the sequence through which the pusher that is holding the OSO stack changes from one to the other.

Figure 2B:
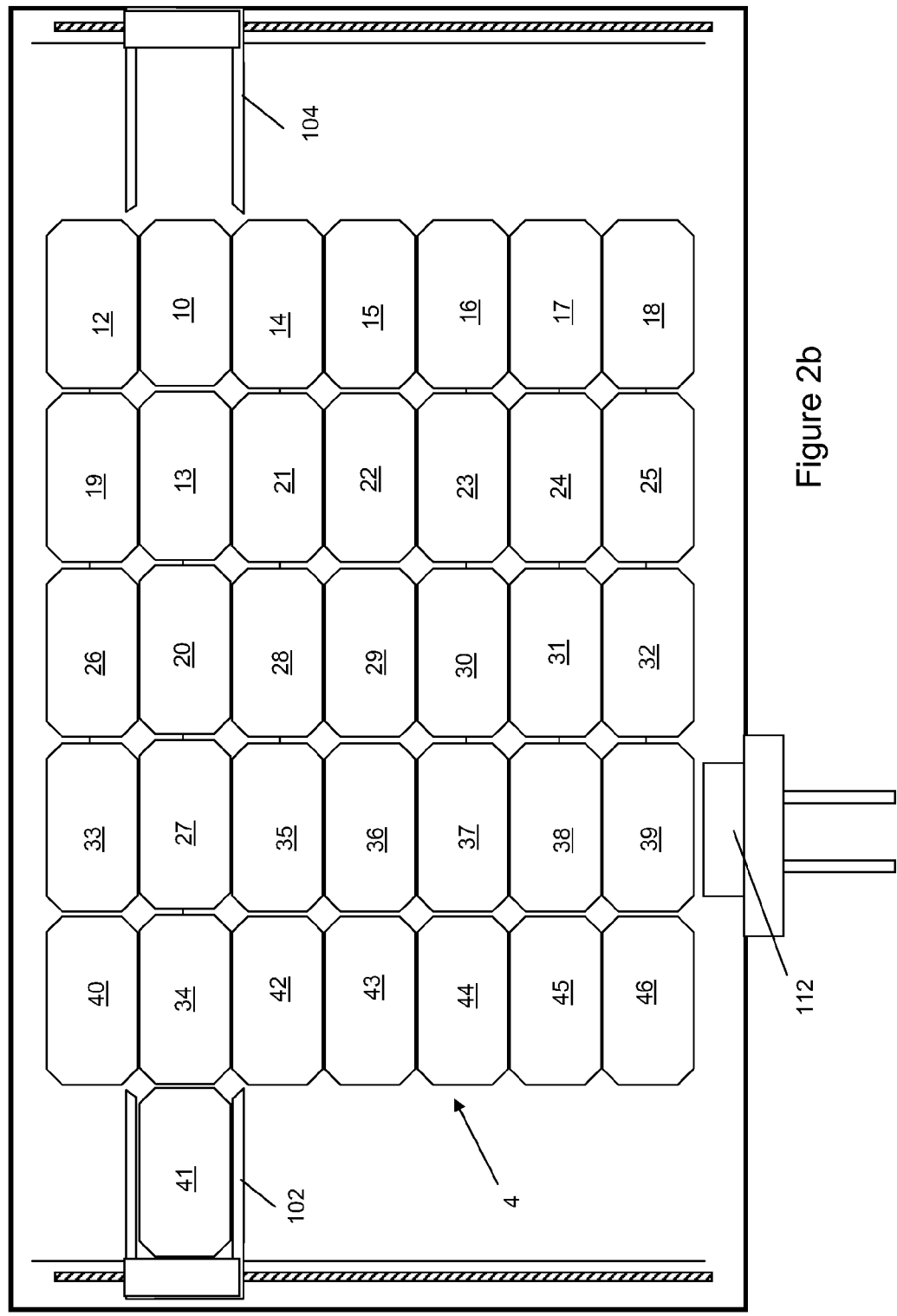
Figure 2C:
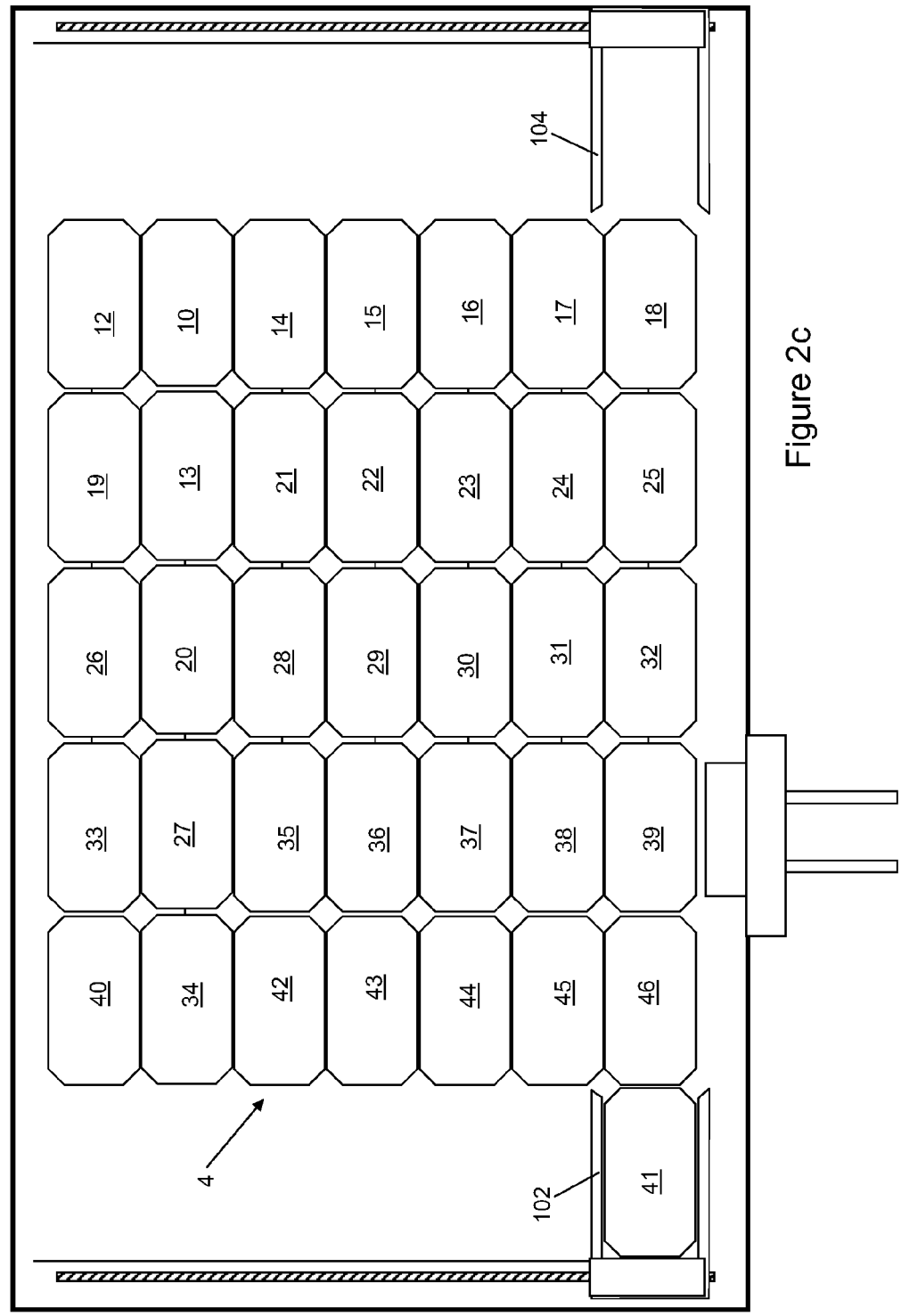
Figure 2D:
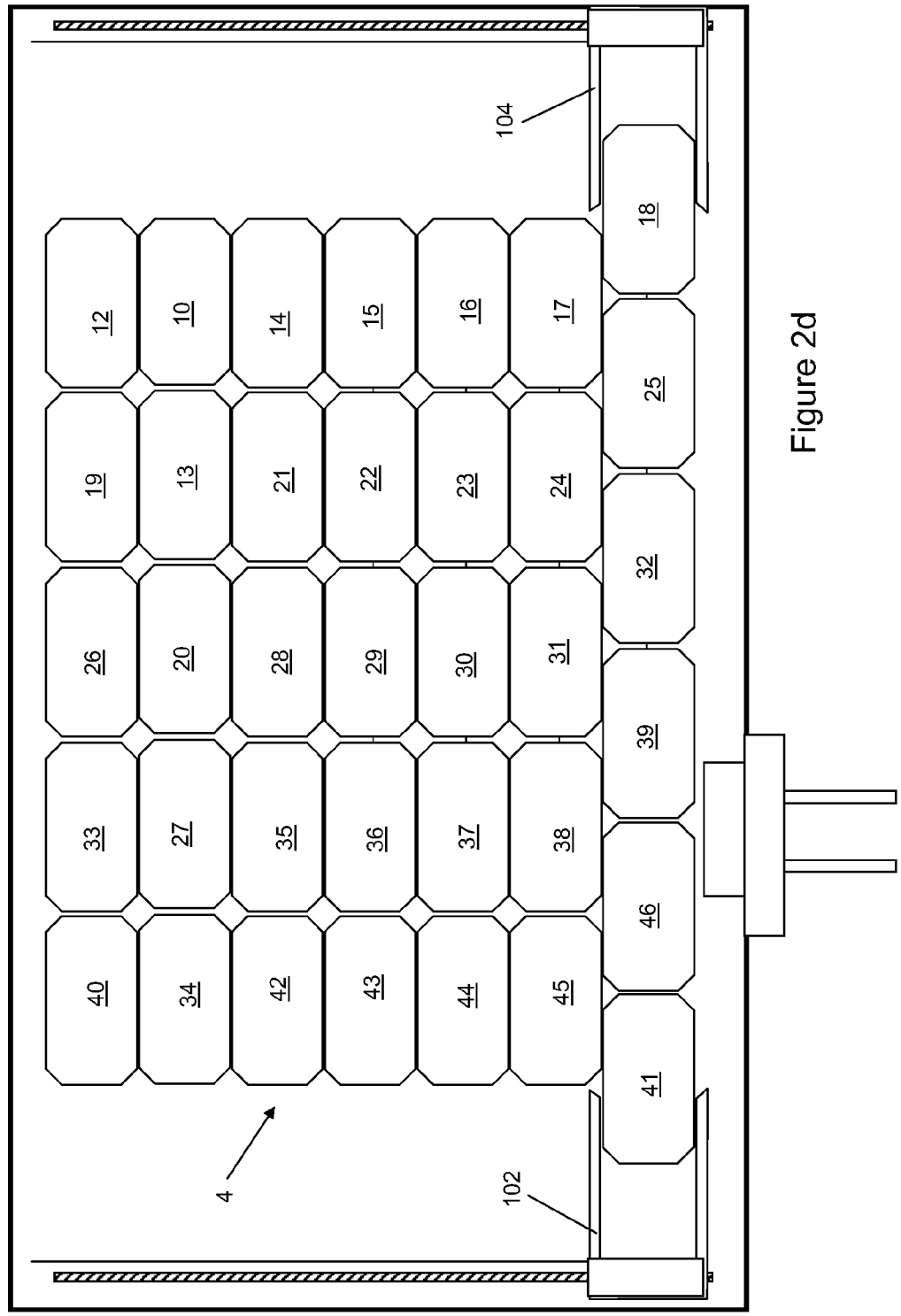
Figure 2E:
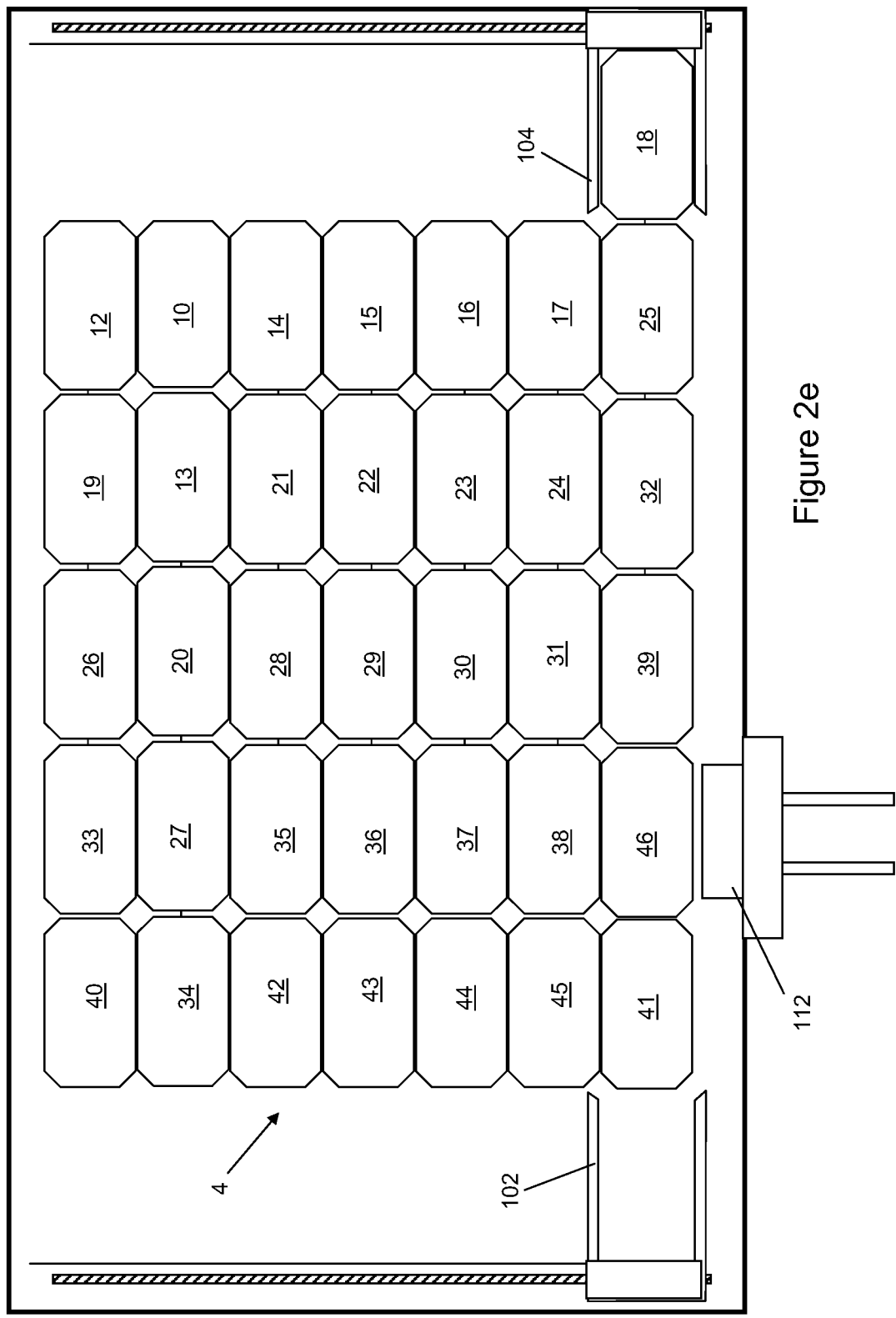

In an exemplary sequence, the system controller receives instructions from a system user to retrieve a sample that is located in stack 41. Starting with the starting stack 10 (in pusher 104) in FIG. 1, pushers 102 and 104 are aligned with row Y6. In FIG. 21, pusher 104 begins to push stack 10 into the right end of row Y6, sliding the entire row and forcing stack 41 into pusher 102, as shown in FIG. 2b. Pushers 102 and 104 are moved toward the front of the storage compartment 2 by drive screw (or cable) 110 and 106, respectively, so that the pushers are aligned with row Y1, shown in FIG. 2c. Pusher 102 pushes stack 41 into the end of row Y1, forcing stack 18 into pusher 104. Following a similar sequence of steps that are not separately illustrated, the pushers 102, 104 move toward the back of the stack array 4 to align with a different row, say row Y2, where pusher 104 pushes stack 18 to force stack 45 into pusher 102. The pushers again move toward the front of the array 4, where pusher 102 pushes stack 45 against the end of row Y1, moving stack 41 into the access position and forcing stack 25 into pusher 104. The system controller will track each movement so that at any given time, the location of each tray (and sample) can be determined.

Figure 3A:
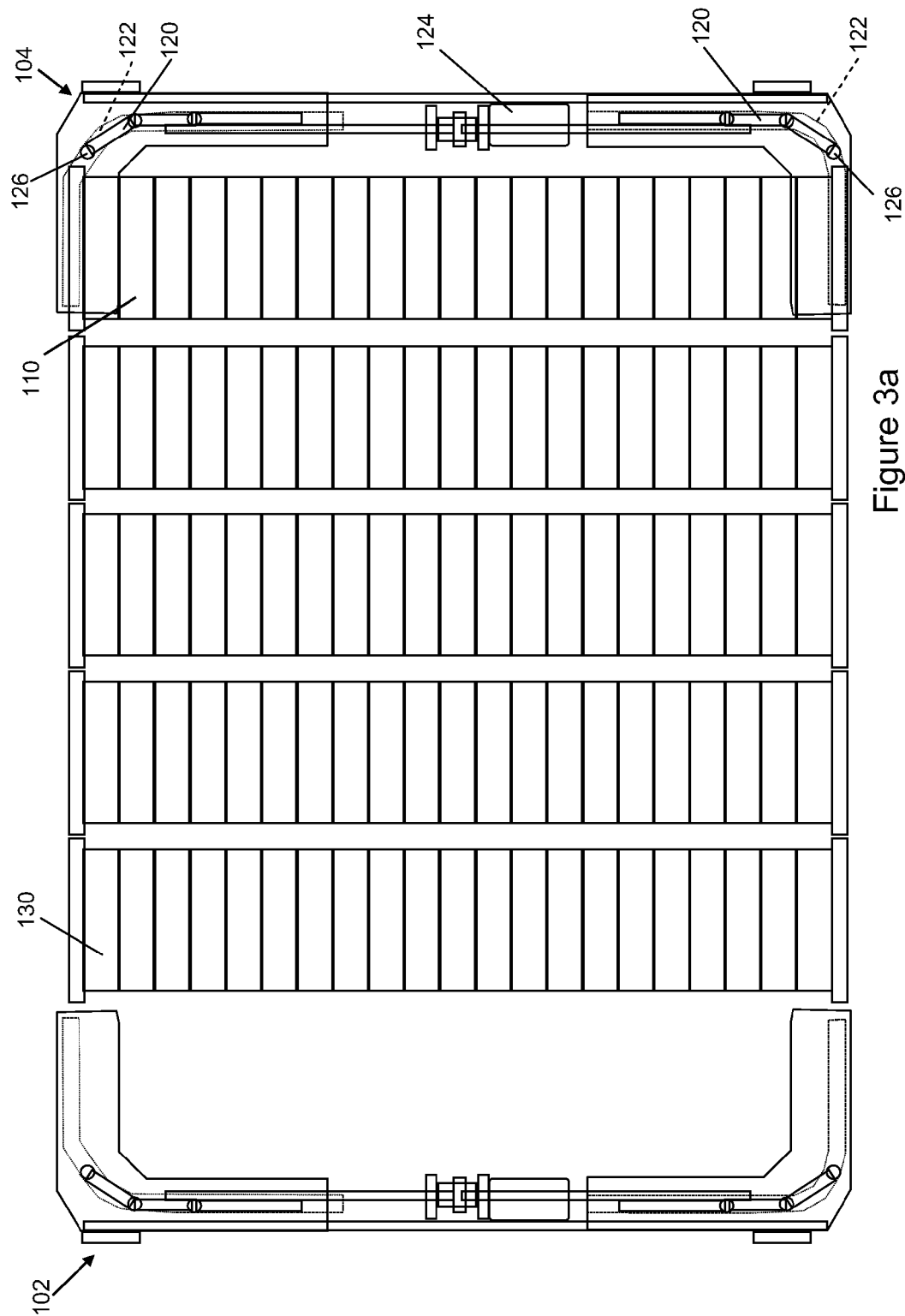
FIGS. 3a-3c are diagrammatic front views of a 4 stack storage array.
Figure 3B:
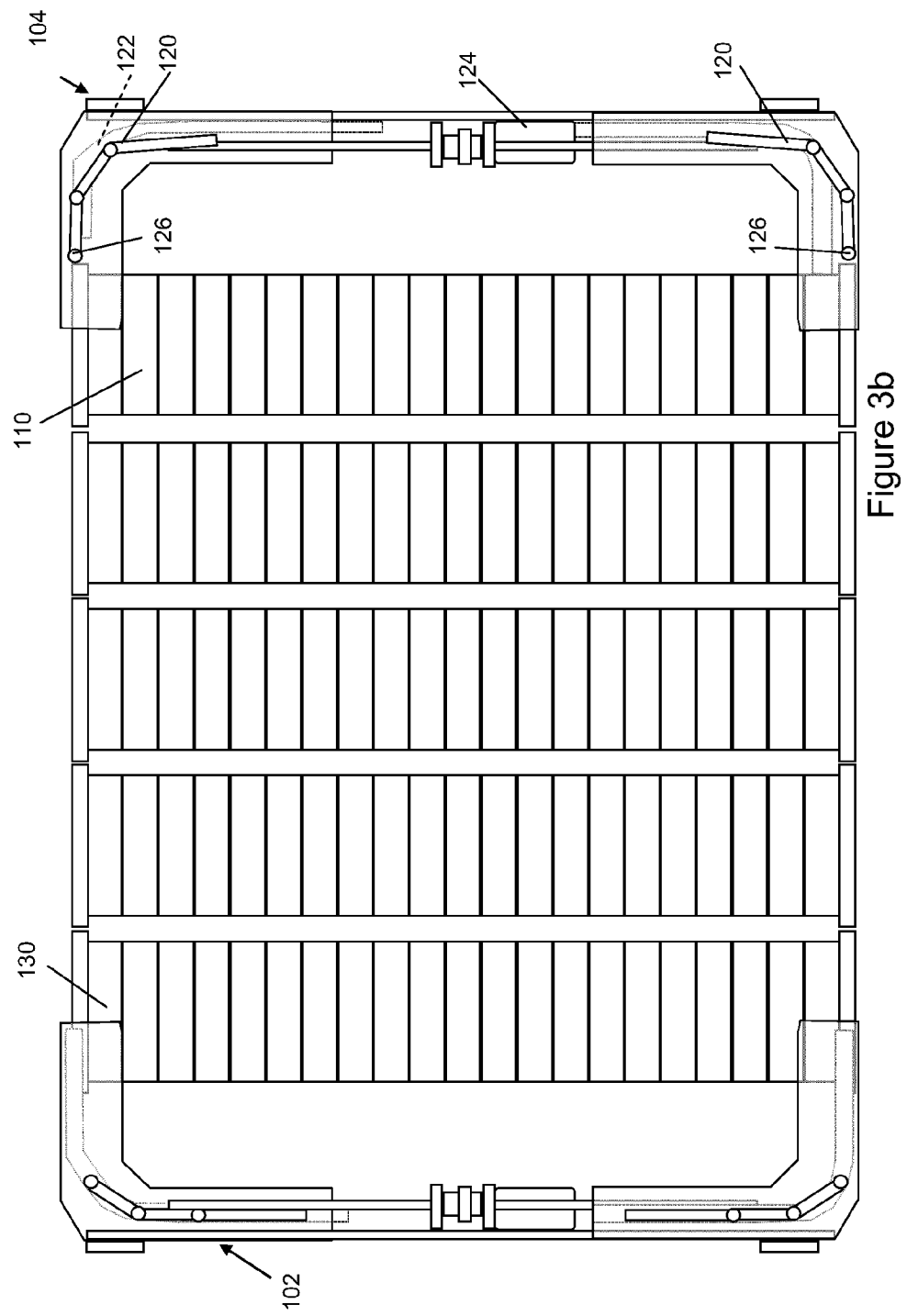
Figure 3C:
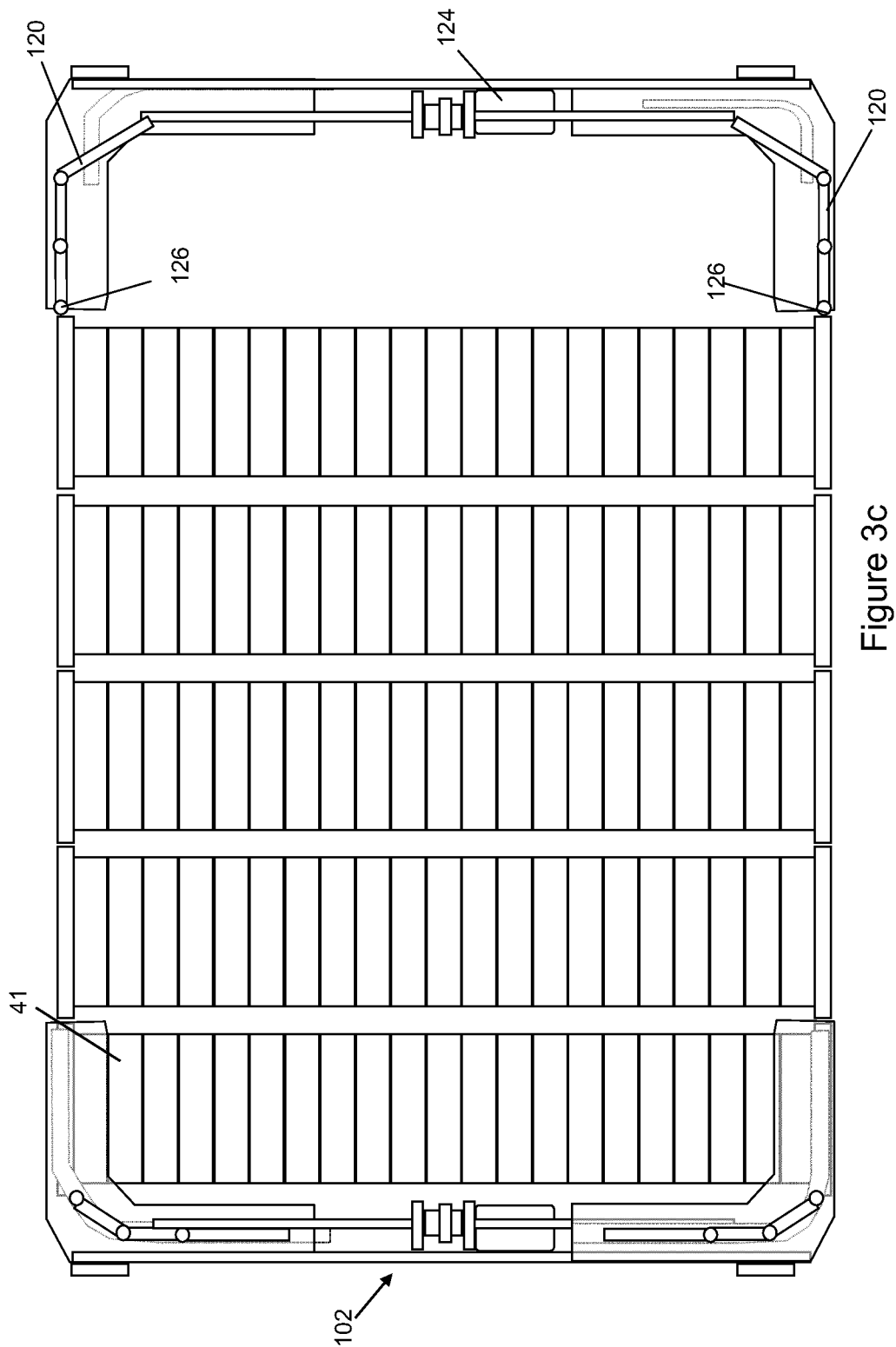

FIGS. 3a-3c are diagrammatic front views of a four stack storage array with pushers 102 and 104 showing the transfer progression of a starter stack 110, which is initially held by pusher 104 in FIG. 3a. Articulated pusher arms 120 at the top and bottom of pusher 104 are activated by the pusher 104 drive motor 124, causing the pusher arms to move within channels 122 so that the distal ends 126 to extend toward and contact the top and bottom plates of the starter stack 110, shown in FIG. 3b. As the pusher arms 120 continue to extend, the starter stack 110 is pushed away from pusher 104 and toward the storage array, contacting the closest stack to push the entire row toward pusher 102 and moving starter stack 110 into the storage array, shown in FIG. 3c. FIG. 3c shows the pusher arms 120 of pusher 104 fully extended while the stack 130 that was being pushed is fully received in pusher 102. Although not separately numbered in the figures, the pusher mechanism of pusher 102 includes the same components that are shown in pusher 104 in a mirror image configuration.

FIG. 4a is a diagrammatic front view showing the drive details of the pusher arms 120. As shown in detail FIG. 4b, the drive motor 124 is attached via a belt 125, chain or other drive linkage to a rotating toothed cylinder 132. The toothed cylinder 132 drives the toothed ends of a pair of screw drives 134 that extend in both directions, upward and downward, from the toothed cylinder. The screw drives 134 are connected to the proximal ends of the articulated arms 120, causing them to extend outward or retract inward when the drive motor is activated. The upper and lower guide arms 140 of the pusher fit over the top and bottom plates of the stacks, respectively, to ensure stability and even application of force when the stacks are moved.

Figure 5:
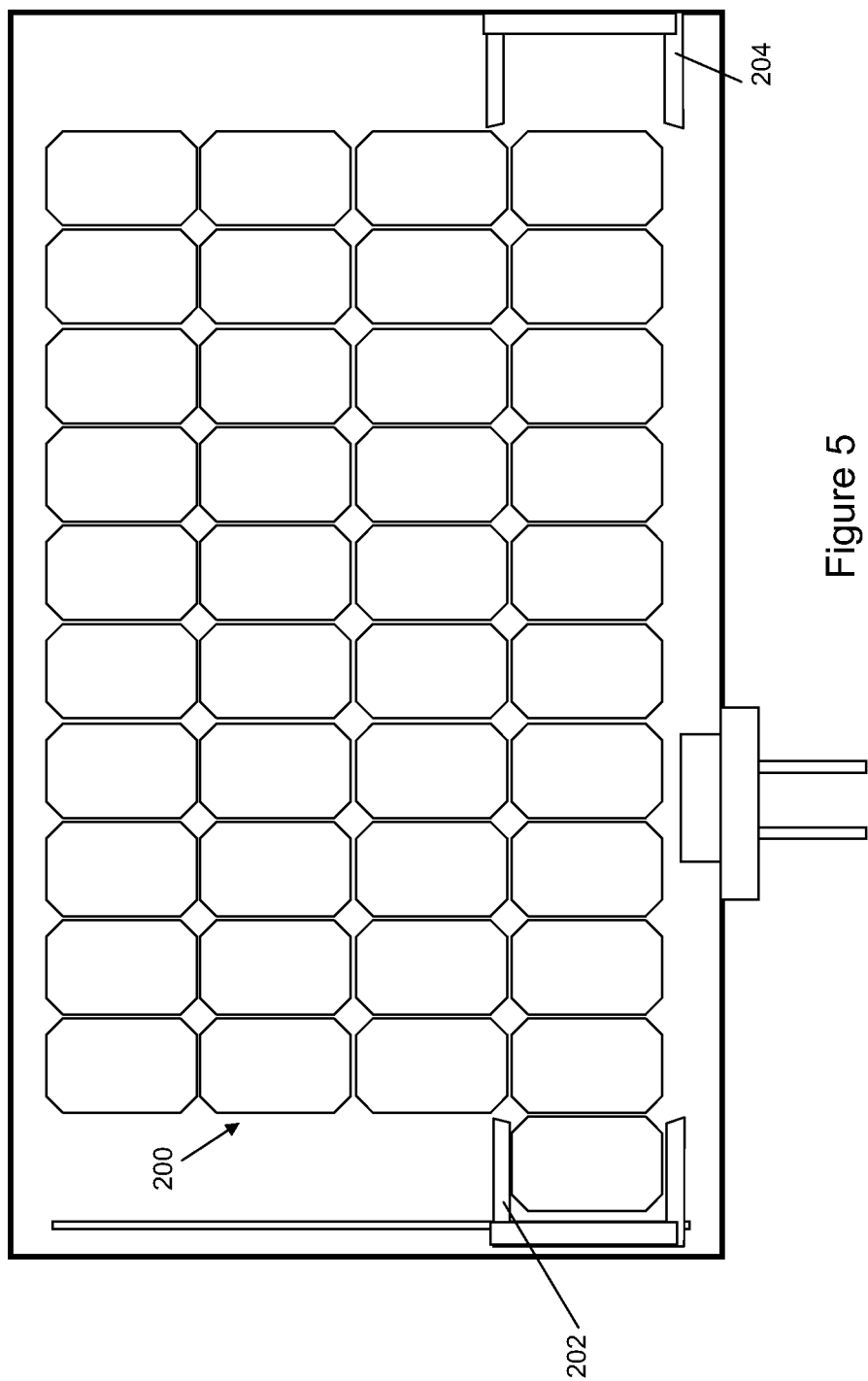
FIG. 5 is a diagrammatic top view of a storage array with a stack arrangement with additional columns.

FIG. 5 is a diagrammatic top view of a storage array 200 with a stack arrangement with additional columns that provides a denser storage option. Operation of the robots 202 and 204 is the same as that described previously for the embodiments of FIGS. 1-4, however, additional transfers may be required to reach a desired stack.

Figure 6:
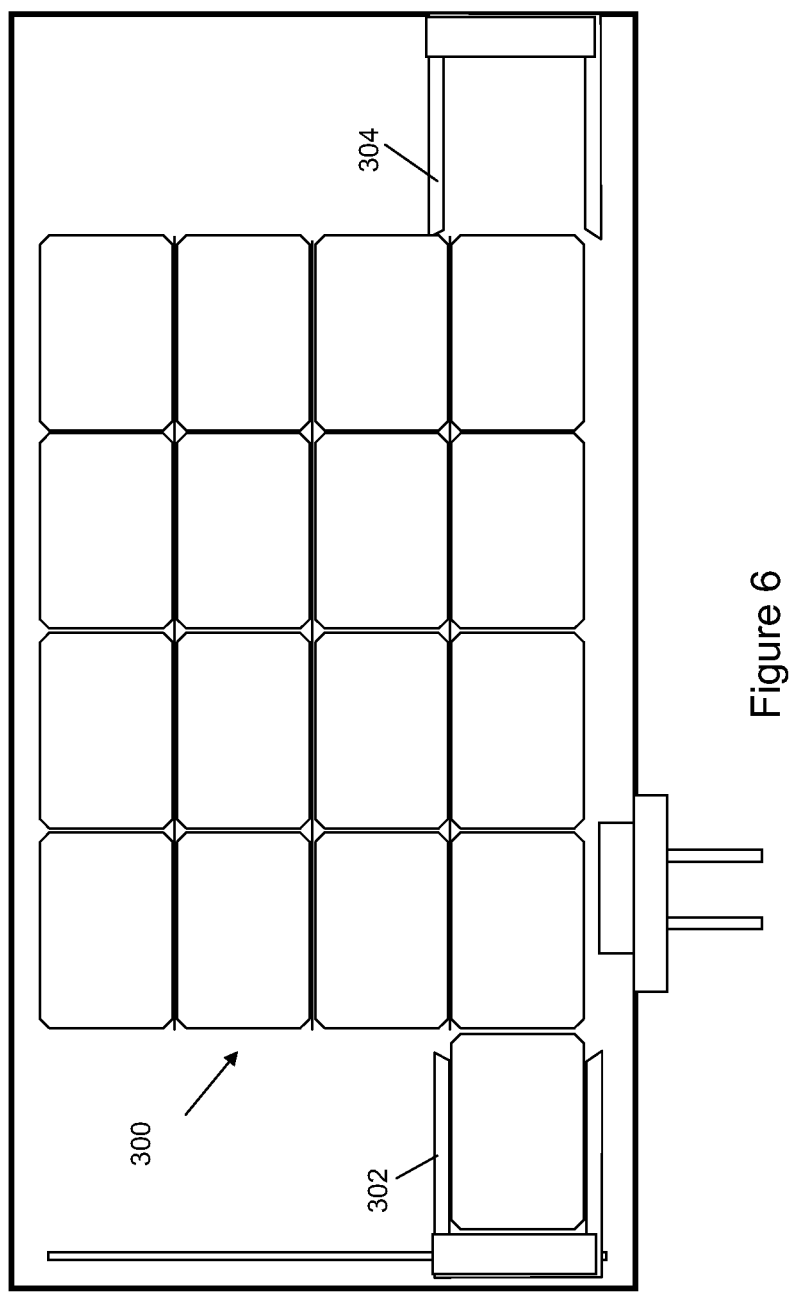
FIG. 6 is a diagrammatic top view of a storage array according to the present invention with double-wide stacks.

FIG. 6 is a diagrammatic top view of a storage array 300 with double-wide stacks that permit denser storage without requiring additional steps that would be required for rows having a larger number of stacks. Again, the robots 302 and 304 operate in the same manner as described above.

The inventive system provides a significant improvement upon the conventional narrow aisle approach to sample storage by eliminating the aisle(s) between the shelves, thus increasing the storage capacity for a given footprint.

The invention claimed is:

1. A storage system for storing a plurality of samples, comprising:
    a storage compartment having an access port;
    an array of stacks disposed within the storage compartment, the array of stacks comprising rows and columns of slidable stacks adapted for retaining sample containers, each stack being formed of sample containers disposed along stacked layers where the stacked layers are transverse to the rows and columns;
    a plurality of guides extending along each row of stacks adapted for sliding the stacks parallel to the rows;
    a pair of robotic handlers disposed on opposite sides of the array of stacks, each robotic handler having a pushing mechanism;
    a drive mechanism for moving the pair of robotic handlers in a direction parallel to the columns; and
    a starter stack retained within a first robotic handler of the pair of robotic handlers;
    wherein the first robotic handler initiates a first push cycle by pushing the starter stack against a first end of a selected row of stacks so that a second stack on the second end of the row of stacks is received by the second robotic handler, the pair of handlers moves to a different row of stacks where the second robotic handler initiates a second push cycle by pushing the second stack into the second end of the different row, wherein the stacked layers of each stack are moved as a unit and the pair of robotic handlers repeat a plurality of push cycles until a selected stack containing a selected sample is positioned for access at the access port.

2. The storage system of claim 1, further comprising a low friction surface disposed below the array of stacks.

3. The storage system of claim 1, where the pushing mechanism comprises:
    a guide arm disposed at each of a top and bottom of a handler assembly, the guide arms being spaced apart to receive a stack therebetween;
    an articulated arm disposed within a channel within each guide arm;
    a screw drive connected to a proximal end of each articulated arm for extending or retracting the articulated arm;

a drive motor for driving the screw drives to simultaneously extend or retract the articulated arms;

wherein the articulated arms are adapted to, when extended, contact a top and a bottom of a stack to be pushed and to push the stack away from the handler assembly and against a row of stacks in the array of stacks.

4. The storage system of claim 1, further comprising a lift mechanism disposed at the access port, the lift mechanism adapted to remove a sample container containing the selected sample from the selected stack.

5. A storage system for storing a plurality of samples, comprising:

a storage compartment having an access port;

an array of stacks disposed within the storage compartment, the array of stacks comprising rows and columns of slidable stacks adapted for retaining sample containers, each stack being formed of sample containers disposed along stacked layers were the stacked layers are transverse to the rows and columns;

a plurality of guides extending along each row of stacks adapted for sliding the stacks parallel to the rows;

a first robotic handler and a second robotic handler disposed on opposite sides of the array of stacks, each robotic handler comprising a pushing mechanism;

a drive mechanism for moving the first and second robotic handlers between the rows of stacks; and a starter stack retained within the first robotic handler;

wherein the first robotic handler initiates a push cycle by pushing the starter stack against a first end of a selected row of stacks to displace a second stack from the selected row of stacks into the second robotic handler, and wherein the stacked layers of each stack are moved as a unit and the first and second robotic handlers execute a series of push cycles on different rows of stacks to reposition a selected stack from its starting location to a different location that is accessible from the access port.

6. The storage system of claim 5, further comprising a low friction surface disposed below the array of stacks.

7. The storage system of claim 5, where the pushing mechanism comprises:

a guide arm disposed at each of a top and bottom of a handler assembly, the guide arms being spaced apart to receive a stack therebetween;

an articulated arm disposed within a channel within each guide arm;

a screw drive connected to a proximal end of each articulated arm for extending or retracting the articulated arm;

a drive motor for driving the screw drives to simultaneously extend or retract the articulated arms;

wherein the articulated arms are adapted to, when extended, contact a top and a bottom of a stack to be pushed and to push the stack away from the handler assembly and against a row of stacks in the array of stacks.

8. The storage system of claim 5, further comprising a lift mechanism disposed at the access port, the lift mechanism adapted to remove a sample container containing the selected sample from the selected stack.

* * * * *